United States Patent
Lee (10) Patent No.: US 10,449,081 B2
(45) Date of Patent: Oct. 22, 2019

(54) OSTOMY APPARATUS

(71) Applicant: Choon Kee Lee, Denver, CO (US)

(72) Inventor: Choon Kee Lee, Denver, CO (US)

( * ) Notice: Subject to any disclaimer, the term of this patent is extended or adjusted under 35 U.S.C. 154(b) by 446 days.

(21) Appl. No.: 15/436,786

(22) Filed: Feb. 18, 2017

(65) Prior Publication Data
US 2018/0235800 A1    Aug. 23, 2018

(51) Int. Cl.
*A61F 5/44* (2006.01)
*A61F 5/445* (2006.01)
*A61F 5/448* (2006.01)

(52) U.S. Cl.
CPC ............ *A61F 5/445* (2013.01); *A61F 5/4405* (2013.01); *A61F 5/4407* (2013.01); *A61F 2005/4486* (2013.01)

(58) Field of Classification Search
CPC combination set(s) only.
See application file for complete search history.

(56) References Cited

U.S. PATENT DOCUMENTS

| | | |
|---|---|---|
| 3,081,771 A | 3/1963 | Lee |
| 4,460,363 A | 7/1984 | Steer et al. |
| 4,592,750 A | 6/1986 | Kay |
| 4,723,952 A | 2/1988 | Esposito |
| 4,826,495 A | 5/1989 | Petersen |
| 4,950,223 A * | 8/1990 | Silvanov ............... A61F 5/441 128/DIG. 25 |
| 5,045,052 A | 9/1991 | Sans |
| 5,941,860 A * | 8/1999 | Wheeler ............... A61F 5/451 604/327 |
| 6,689,111 B2 * | 2/2004 | Mulhauser ............ A61F 5/445 604/332 |
| 7,101,357 B2 | 9/2006 | Tanaka et al. |
| 7,300,399 B2 * | 11/2007 | Bonadio ............ A61B 17/0293 600/208 |
| 7,951,076 B2 * | 5/2011 | Hart ................... A61B 17/0293 600/206 |
| 8,070,737 B2 * | 12/2011 | Cline .................... A61F 5/445 128/887 |
| 8,105,298 B2 | 1/2012 | Mullejans et al. |
| 8,460,259 B2 * | 6/2013 | Tsai ...................... A61F 5/448 604/335 |
| 8,657,799 B2 * | 2/2014 | Carrubba .............. A61F 5/445 604/318 |
| 8,821,464 B2 * | 9/2014 | Hanuka ................. A61F 5/445 604/333 |
| 9,033,944 B2 | 5/2015 | Wolrich |
| 2003/0187393 A1 * | 10/2003 | Cline .................... A61F 5/445 604/131 |
| 2006/0206069 A1 * | 9/2006 | Cline .................... A61F 5/445 604/337 |

(Continued)

FOREIGN PATENT DOCUMENTS

| | | |
|---|---|---|
| CN | 201190000461 | 6/2013 |
| CN | 102596114 B | 10/2014 |

(Continued)

*Primary Examiner* — Tatyana Zalukaeva
*Assistant Examiner* — Guy K Townsend (57) ABSTRACT

The present invention provides an ostomy apparatus which is capable of reversibly closing and opening an outlet of the ostomy apparatus. The outlet of the ostomy apparatus comprises a stretchable elastomeric tubular wall having a double wall tube-in-tube configuration.

5 Claims, 6 Drawing Sheets

(56) References Cited

U.S. PATENT DOCUMENTS

| | | | |
|---|---|---|---|
| 2007/0088300 A1* | 4/2007 | Cline | A61F 5/445 604/342 |
| 2007/0129695 A1* | 6/2007 | Blum | A61F 5/445 604/338 |
| 2008/0119804 A1 | 5/2008 | Cline et al. | |
| 2011/0106032 A1* | 5/2011 | Kratky | A61F 5/445 604/337 |
| 2011/0282311 A1* | 11/2011 | Nishtala | A61M 1/0019 604/332 |
| 2012/0109086 A1* | 5/2012 | Tsai | A61F 5/448 604/335 |
| 2012/0123361 A1 | 5/2012 | Johansson et al. | |
| 2012/0179124 A1* | 7/2012 | Nguyen-Demary | A61F 5/448 604/333 |
| 2012/0245535 A1 | 9/2012 | Jacobsson et al. | |
| 2013/0079737 A1* | 3/2013 | Hanuka | A61F 5/445 604/318 |
| 2013/0304008 A1* | 11/2013 | Hanuka | A61F 5/4401 604/334 |
| 2014/0364823 A1* | 12/2014 | Nguyen-Demary | A61F 5/448 604/333 |
| 2015/0141944 A1* | 5/2015 | Hanuka | A61F 5/4401 604/337 |
| 2016/0228284 A1* | 8/2016 | Carrubba | A61F 5/448 |

FOREIGN PATENT DOCUMENTS

| | | |
|---|---|---|
| CN | 105413007 A | 3/2016 |
| DE | 19653974 B4 | 10/2004 |
| EP | 0653196 A1 | 5/1995 |
| ES | 2369209 T3 | 11/2011 |
| KR | 101482496 B1 | 1/2015 |

\* cited by examiner

OSTOMY APPARATUS

CROSS REFERENCE TO RELATED APPLICATIONS

Attached please refer to the Information Disclosure Statement for the cross reference to related applications.

TECHNICAL FIELD

The present invention relates generally to the field of draining body fluids and solids from human body through an ostomy. More specifically, the present invention provides an ostomy apparatus for reversible opening and closure of the ostomy apparatus.

BACKGROUND OF THE INVENTION

Artificial medical devices such as colostomy or ileostomy are indicated if a patient undergoes a drainage procedure following removal of a part of a normal anatomic structure like a loop of small or large bowel. Oftentimes the drainage procedures are temporary but in not so rare instances it could be for permanent placement. Of a few issues related to attachment of an artificial device to a human body, loss of voluntary control of the drainage has been a significant and contentious issue for all patients. For an example, stool needs to stay in the large bowel for a sufficient time to let water and other ingredients of the stool to be absorbed back to the human body. Disposal of the stool outside the human body through the colostomy device is not a controlled process in that whenever there are antegrade propulsive contractions of the large bowel, there will be an aliquot of stool coming out. Consequently the colostomy device needs to be an open system for drainage at all time. Although some devices are available for voluntary control of the stool drainage, a majority of them use a simple lid to close a drainage outlet of the colostomy. Issues of the use of the simple lid are painfully apparent in that a patient using the lid based colostomy needs to manually open and drain the stool into a drainage bag, running a risk of spilling the stool around patient's body and clothing.

An air-filled tubular balloon can be twisted along an axial center of the tubular balloon to make a tubular segment closed and separated from adjacent tubular segments of the tubular balloon. It can be applied to a double-walled elastomeric tubular conduit which is twisted along an axial center of the double-walled elastomeric tubular conduit. Upon the axial twisting of the double-walled elastomeric tubular conduit, a finite amount of air trapped in between an outer tubular wall and an inner tubular wall of the double-walled tubular conduit balloons out a trapped portion of the double-walled elastomeric tubular conduit. The outer and inner tubular walls of the double-walled elastomeric tubular conduit reversibly become a valve closing the double-walled tubular conduit upon the axial twisting. The trapped air in the ballooned and trapped portion exerts a centripetal pressure toward the axial center of the double-walled elastomeric tubular conduit which is the center of the axial twisting. The centripetal pressure is configured to tighten the center of the axial twisting to a degree that a contractile pressure coming from the large bowel on a portion of the stool can be resisted.

SUMMARY OF THE INVENTION

In one embodiment, the present invention provides an ostomy apparatus in a modular configuration comprising four individual components, including a base assembly, a reversible valve assembly having a pair of rotatable disks and a double-walled elastomeric tube, a cap, and a collection bag. The base assembly is configured with a circular connecting rim having a central hole affixed to an attachment sheet of the base assembly. A proximal portion of the double-walled elastomeric tube of the reversible valve assembly is fixedly attached to a first rotatable disk of the reversible valve assembly. The first rotatable disk is configured to reversibly and sealably couple with the circular connecting rim of the base assembly. A distal portion of the double-walled elastomeric tube is fixedly attached to a second rotatable disk of the reversible valve assembly. The second rotatable disk is configured to reversibly and fastenably couple with the first rotatable disk. Fastenable coupling of the second rotatable disk with the first rotatable disk requires twisting of the second rotatable disk along an axial center a longitudinal axis of the double-walled elastomeric tube over a few revolutions about the axial center. The fastenable coupling of the second rotatable disk with the first rotatable disk makes the double-walled elastomeric tube concentrically collapsed and flattened to a right angle to the longitudinal axis of the double-walled elastomeric tube in a twisted and closed configuration.

In one embodiment, a surface area of the attachment sheet of the base assembly is configured to be at least four times larger than an area of the central hole inside the circular connecting rim. The attachment sheet has a central hole which corresponds to the central hole of the circular connecting rim. The attachment sheet of the base assembly is configured to reversibly adhere to a skin around an ostomy site and to be able to resist a forward contractile pressure of a bowel without detachment of the ostomy apparatus having the reversible valve assembly in a closed configuration from the skin. Resistance of the ostomy apparatus with the reversible valve assembly in the closed configuration to the forward contractile pressure of the bowel is proportional to the surface area of the attachment sheet which adheres to the skin around the ostomy site.

In one embodiment, the circular connecting rim of the base assembly is provided in a snap-in configuration which allows the first rotatable disk of the reversible valve assembly to reversibly and fastenably couple with a plurality of female couplers of the circular connecting rim. A leakproof elastomeric circular gasket is placed in between the circular connecting rim and the first rotatable disk, in order to seal off a gap between the circular connecting rim and the first rotatable disk and to prevent spillage of liquid biologic materials through the gap. The leakproof elastomeric gasket is fixedly adhered to a top surface of the circular connecting rim, facing a surface of the first rotatable disk which contacts the leakproof elastomeric gasket. In another embodiment, the circular connecting rim is configured to reversibly and sealably couple with a connecting port of the collection bag. The connecting port of the collection bag is provided in a configuration similar to the first rotatable disk for interchangeable leakproof coupling with the circular connecting rim.

In one embodiment, the reversible valve assembly is provided in a tubular configuration and comprises the double-walled elastomeric tube fixedly connected to the first rotatable disk on one end and to the second rotatable disk on the other end of the double-walled elastomeric tube. The double-walled elastomeric tube is provided in a tube-in-tube configuration having an outer tube slidably placed over an inner tube. In between the outer tube and the inner tube, there is provided a closed space bordered by an inner surface of the outer tube, an outer surface of the inner tube, and the first and the second rotatable disks fixedly attached to each end of the double-walled elastomeric tube, respectively. The closed space is configured to contain gas such as air. The outer tube and the inner tube of the double-walled elastomeric tube are made of an elastomeric membrane and are configured to be stretchable and twistable.

In one embodiment, the rotatable disk of the reversible valve assembly is provided in a ring configuration having a circular rim surrounding a hole. The hole is open to and coaxially aligned with a tubular space of the double-walled elastomeric tube. The circular rim of the rotatable disk is configured with a plurality of male couplers which is configured to reversibly and fastenably mate with the female couplers of the circular connecting rim of the base assembly, and with female couplers of the other rotatable disk, of the cap and of the collection bag. A circular margin of the doubled-walled elastomeric tube is fixedly adhered to the circular rim in a way the circular margin is not to be torn apart on axial twisting of the rotatable disk over several revolutions about the axial center along the longitudinal axis of the reversible valve assembly.

In one embodiment, the second rotatable disk is configured to be axially twistable over several revolutions about the axial center along the longitudinal axis of the reversible valve assembly while the first rotatable disk is fastened to the circular connecting rim of the base assembly. Upon the axial twisting of the second rotatable disk, the double-walled elastomeric tube is twisted about the axial center along the longitudinal axis of the reversible valve assembly in a way an upper half of the double-walled elastomeric tube is circumferentially squeezed and flattened at the right angle to the longitudinal axis of the reversible valve assembly. In this way, the squeezed upper half of the double-walled elastomeric tube closes the tubular space of the double-walled elastomeric tube. The closed space then is bordered by the inner surface of the outer tube, the outer surface of the inner tube, and the first and the second rotatable disks. The closed space becomes pressurized as the axial twisting of the double-walled elastomeric tube proportionally shrinks the closed space upon each revolution of the axial twisting. The pressurized closed space exerts an outward pressure on the axial center and on the inner surface of the outer tube, and the outer surface of the inner tube. The outward pressure on the axial center is configured to tighten the axial center in a way the upper half of the double-walled elastomeric tube closing the tubular space can withstand the forward contractile pressure from the bowel. Similar processes are expected of a lower half of the double-walled elastomeric tube upon the axial twisting of the second rotatable disk while the first rotatable disk remains stationary.

In one embodiment, the rotatable disk of the reversible valve assembly is configured with a plurality of male couplers and a plurality of female couplers disposed on the circular rim. The male couplers are configured to reversibly and fastenably mate with the female couplers of the other rotatable disk of the reversible valve assembly. Following full axial twisting of the double-walled elastomeric tube of the reversible valve assembly, the male couplers of the second rotatable disk reversibly and fastenably couple with the female couplers of the first rotatable disk in a way the double-walled elastomeric tube in the twisted and closed configuration is tightly encased by both the first and second rotatable disks.

In one embodiment, the cap is configured to reversibly close the reversible valve assembly by fastenable coupling with the second rotatable disk and with the base assembly. The cap is provided with a first ring-shaped internal helical thread on a circumferential rim of the cap and a second internal helical thread close to an inner apical portion of the cap corresponding to an external helical thread of the second rotatable disk. The second internal helical thread of the cap is configured to reversibly and fastenably couple with the external helical thread of the second rotatable disk.

In one embodiment, the collection bag is configured to reversibly and sealably couple with the second rotatable disk of the reversible valve assembly. The collection bag is provided with a plurality of the female couplers on a circular rim of the connecting port of the collection bag. The female couplers of the circular rim of the connecting port are configured to reversibly and sealably couple with the male couplers of the second rotatable disk. The collection bag is also configured to reversibly and sealably couple with the base assembly. The plurality of the female couplers on the circular rim of the connecting port of the collection bag are configured to reversibly and sealably couple with the male couplers of the base assembly.

BRIEF DESCRIPTION OF THE DRAWINGS

FIGS. 1A-1D show a schematic illustration of individual components of an ostomy apparatus: FIG. 1A shows a cap configured to reversibly cover a reversible valve assembly shown in FIG. 1B; FIG. 1C shows a base assembly to which the reversible valve assembly is reversibly fastenable; FIG. 1D shown a collection bag configured to reversibly couple with the base assembly of FIG. 1C and with the reversible valve assembly of FIG. 1B.

DETAILED DESCRIPTION OF THE DRAWINGS

As described below, the present invention provides an ostomy apparatus having a reversible valve assembly. It is to be understood that the descriptions are solely for the purposes of illustrating the present invention, and should not be understood in any way as restrictive or limited. Embodiments of the present invention are preferably depicted with reference to FIGS. 1 to 6, however, such reference is not intended to limit the present invention in any manner. The drawings do not represent actual dimension of devices, but illustrate the principles of the present invention.

Figures 1A, 1B, 1C, 1D:
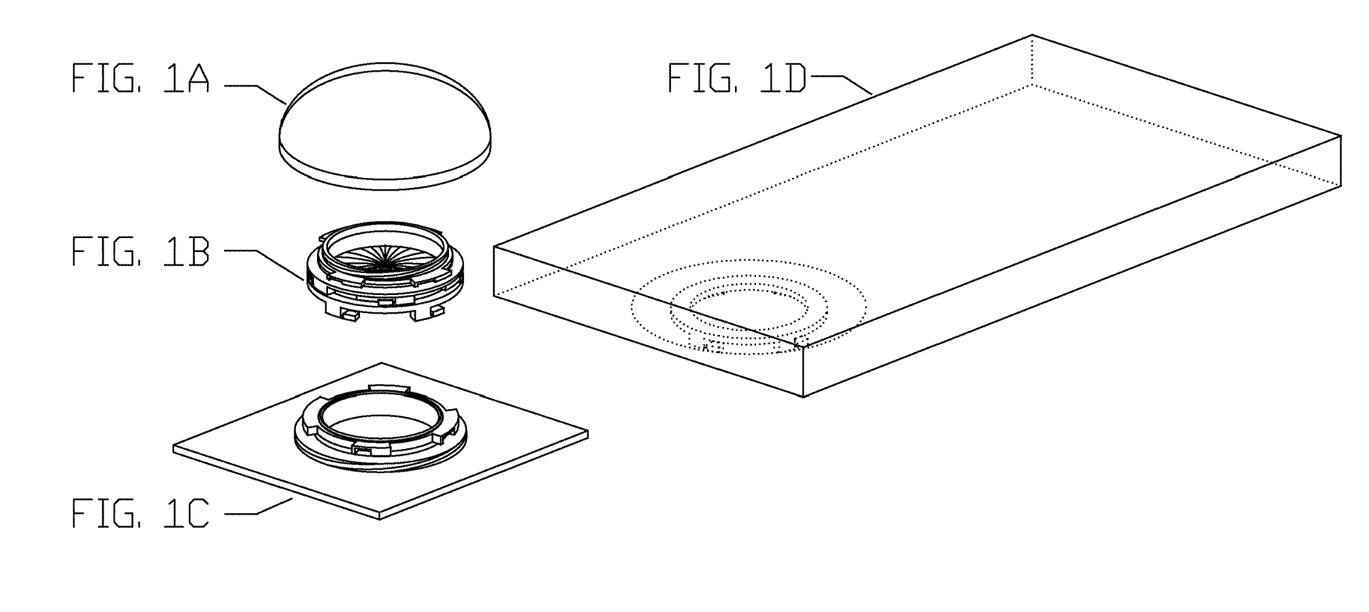

FIGS. 1A-1D show a schematic illustration of individual components of the ostomy apparatus: FIG. 1A shows a cap provided in a hemispherical bowel configuration having an inner circular rim which is configured to reversibly couple with the reversible valve assembly shown in FIG. 1B. The hemispherical bowel configuration having the inner circular rim also allows the cap to couple with a base assembly shown in FIG. 1C. The reversible valve assembly of FIG. 1B is configured to reversibly and sealably couple with the base assembly of FIG. 1C. The reversible valve assembly of FIG. 1B is shown in a collapsed configuration. The configuration of the reversible valve assembly of FIG. 1B allows the reversible valve assembly to reversibly and sealably couple with a collection bag shown in FIG. 1D. The collection bag of FIG. 1D is configured to couple with the base assembly of FIG. 1C and with the reversible valve assembly of FIG. 1B.

Figure 2A:
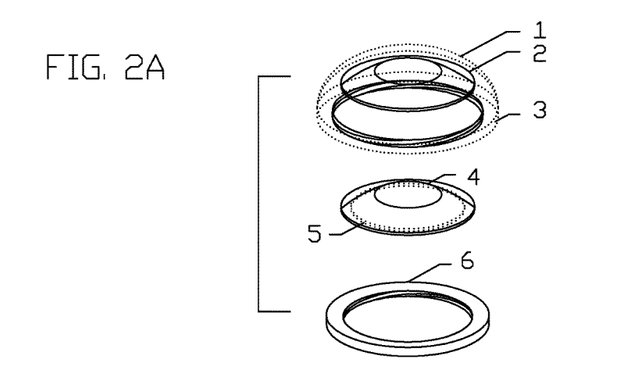
FIGS. 2A-2G represent a schematic exploded view of individual components of the reversible valve assembly.

FIGS. 2A-2G represent a schematic exploded view of individual components of the reversible valve assembly. FIG. 2A shows an outer shell 1 of the hemispherical bowel-shaped cap having an inner apical portion 2 and the circular rim 3. The inner apical portion 2 comprises an inner helical thread 5 disposed on an inner peripheral circumference of the inner apical portion 2 and a dome portion 4. The dome portion 4 is configured to fixedly attach to the inner apical portion 2, thereby providing structural support for the outer shell. A ring-shaped internal helical thread 6 is configured to be inserted in the outer shell 1 in a way the ring-shaped internal helical thread fixedly adheres to an inner surface of the circular rim 3.

FIGS. 2B-2G show the schematic exploded view of the individual components of the reversible valve assembly of FIG. 1B. The reversible valve assembly comprises a first rotatable disk 17 of FIG. 2G, a second rotatable disk 7 of FIG. 2B, and a double-walled elastomeric tube 13 of FIG. 2D. The double-walled elastomeric tube 13 is configured to fixedly adhere to the first rotatable disk of FIG. 2G via a flange portion 16 of FIG. 2F on one tubular end of the double-walled elastomeric tube, and to the second rotatable disk of FIG. 2B via a flange portion 12 of FIG. 2C on the other tubular end of the double-walled elastomeric tube. The double-walled elastomeric tube 13 comprises an outer tube 14 and an inner tube 15 in a tube-in-tube configuration, shown in a see-through view of FIG. 2E. The outer tube 14 is configured to be separated in a distance from the inner tube 5 in a way a space is provided between the outer and inner tubes 14 and 15. The flange portions 12 and 16 are configured to tightly seal both ends of the double-walled elastomeric tube in order to form a closed space between the outer and inner tubes 14 and 15.

Figure 2B:
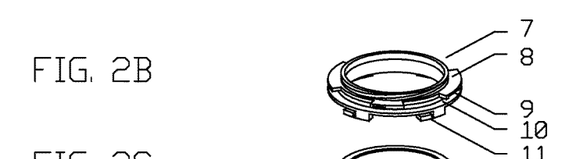
Figures 2C, 2D, 2F:
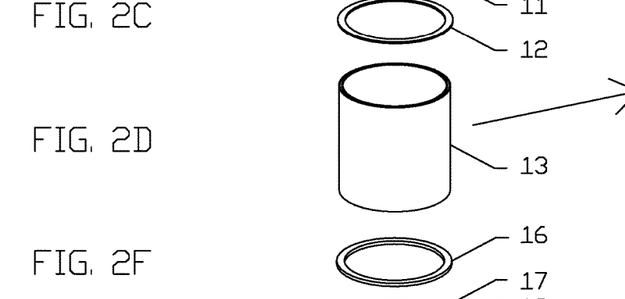
Figure 2E:
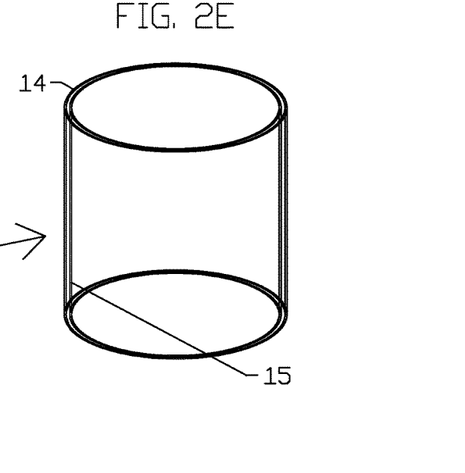
Figures 2G, 2H:
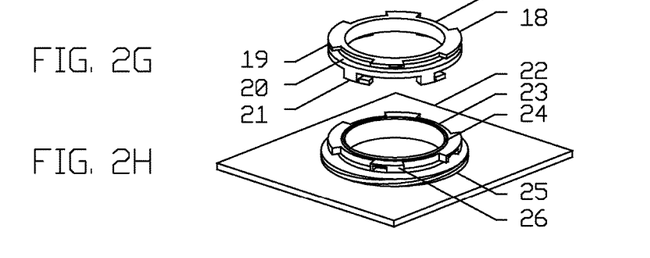
FIG. 2H shows a schematic view of components of the base assembly.

The second rotatable disk 7 of FIG. 2B is provided in a ring configuration comprising a circular rim 10 which has a central hole. The circular rim 10 comprises a plurality of male couplers 11 and a plurality of female couplers 9, with both couplers disposed around the circular rim 10. The plurality of the male couplers 11 are disposed on a surface of the circular rim 10 facing away from the double-walled elastomeric tube 13 of FIG. 2D, whereas the plurality of the female couplers 9 are disposed on an opposite surface of the circular rim 10 facing the double-walled elastomeric tube 13 of FIG. 2D. Similarly, the first rotatable disk 17 of FIG. 2G is provided in the ring configuration comprising a circular rim 20 which has a central hole. The circular rim 20 comprises a plurality of male couplers 21 and a plurality of female couplers 19, with both couplers disposed around the circular rim 20. The plurality of the male couplers 21 are disposed on a surface of the circular rim 20 facing away from the double-walled elastomeric tube 13 of FIG. 2D, whereas the plurality of the female couplers 19 are disposed on an opposite surface of the circular rim 20 facing the double-walled elastomeric tube 13 of FIG. 2D.

FIG. 2H shows a schematic view of components of the base assembly. The base assembly is provided in a ring configuration comprising a circular rim 23 which has a central hole. The circular rim 23 is fixedly attached to an adhesive sheet 22 which coaxially is open to the central hole of the circular rim 23. The adhesive sheet 22 has an adhesive surface disposed on an opposite side to the circular rim 23. The circular rim 23 comprises a plurality of female couplers 26 disposed around the circular rim 10, and a circular external helical thread 25 disposed between the plurality of female couplers 26 and the adhesive sheet 22. On a surface of the circular rim 23 and around a peripheral circumference of the circular rim 23, there is provided an O ring portion 24 which is configured to leakproofly seal a contact between the circular rim 23 and the first rotatable disk 17. The O ring portion 24 fixedly adjoins the circular rim 23.

Figure 3A:
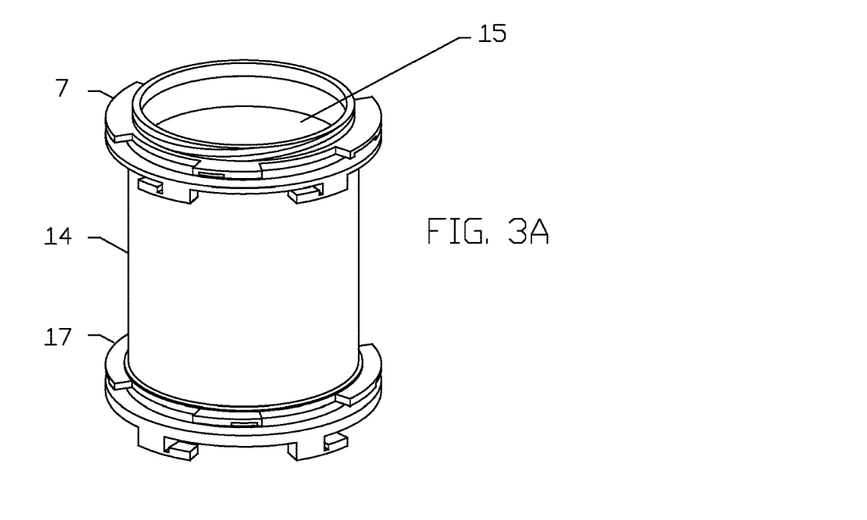
FIGS. 3A-3C illustrate a schematic view of a method of reversible closure of a double-walled elastomeric tube of the reversible valve assembly.
Figure 3B:
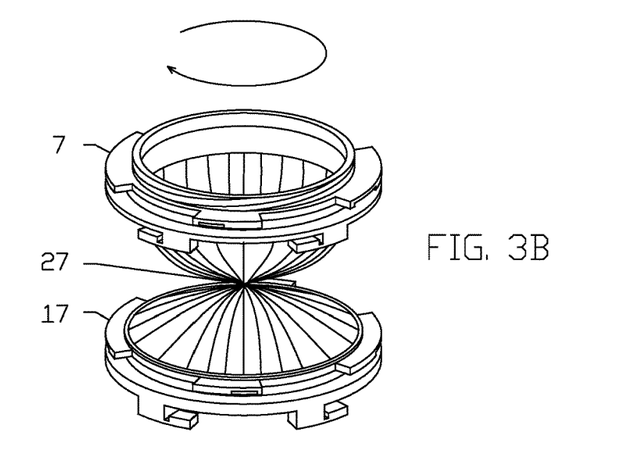
Figure 3C:
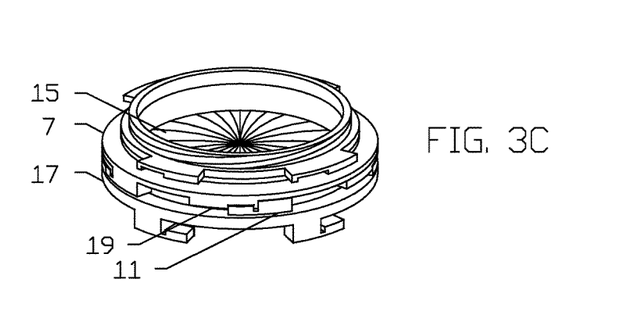

FIGS. 3A-3C illustrate a schematic view of a method of reversible closure of a double-walled elastomeric tube of the reversible valve assembly. In an untwisted and open configuration shown in FIG. 3A, the outer tube 14 and the inner tube 15 the double-walled elastomeric tube of the reversible valve assembly are fixedly attached to the first rotatable disk 17 on one end of the double-walled elastomeric tube and to the second rotatable disk 7 on the other end of the double-walled elastomeric tube. Shown in FIG. 3B, the second rotatable disk 7 is being twisted about an axial center of the double-walled elastomeric tube while the first rotatable disk 17 remains stationary. An axial twist center 27 is formed by the outer and inner tubes in the twisted and closed configuration approximately mid point between the first and the second rotatable disks. The axial twist center 27 is configured to be tightened hard upon several revolutions of the second rotatable disk 7. Following the several revolutions of the second rotatable disk 7, the male coupler 11 of the second rotatable disk 7 reversibly and fastenably couples with the female coupler 19 of the first rotatable disk 17 in a way the coupling of the first rotatable disk 17 with the second rotatable disk 7 produces a concentric reversible valve from the double-walled elastomeric tube, shown in FIG. 3C. In this collapsed configuration of the reversible valve assembly shown in FIG. 3C, the inner tube 15 is in direct contact with and is to resist biologic materials underneath the first rotatable disk 17. Releasing the second rotatable disk 7 from the first rotatable disk 17 reverses the concentric reversible valve back to the double-walled elastomeric tube in an open tubular configuration which then allows transfer of the biologic materials across the double-walled elastomeric tube.

Figure 4A:
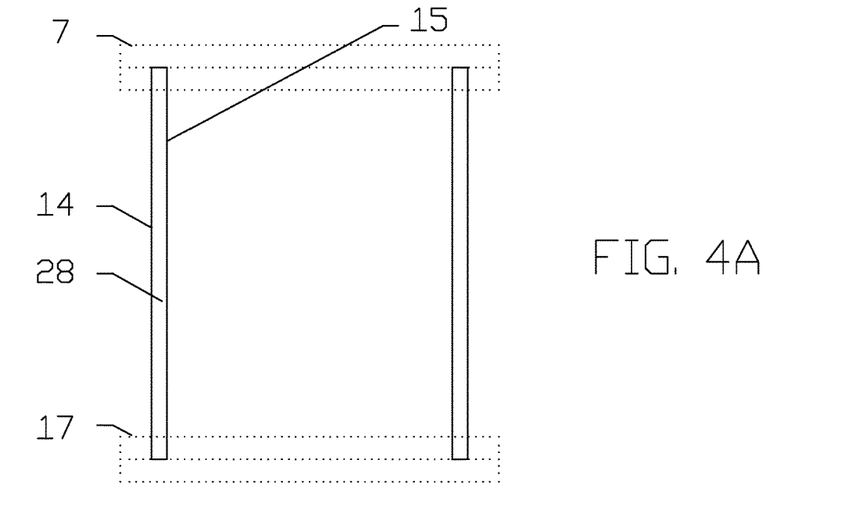
FIGS. 4A-4C depict a schematic see-through cross-sectional view of the double-walled elastomeric tube of the reversible valve assembly in a process of the reversible closure of the double-walled elastomeric tube.
Figure 4B:
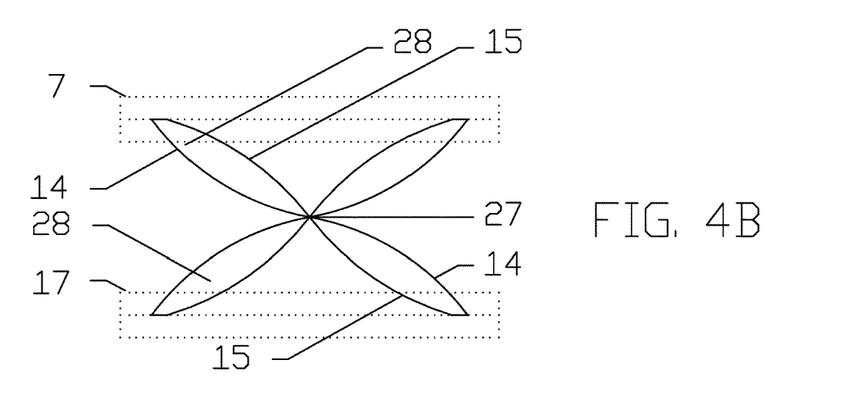
Figure 4C:
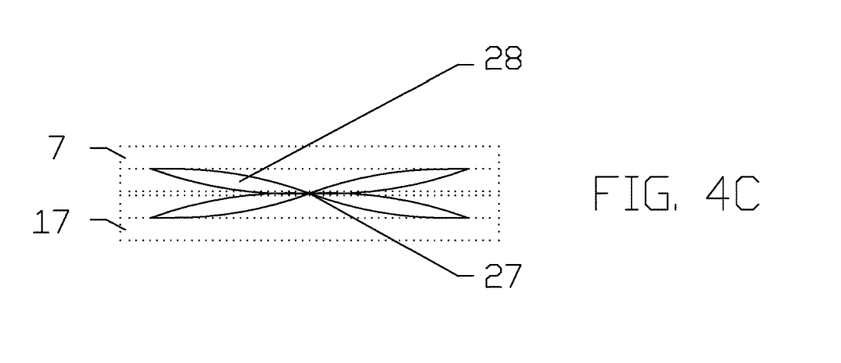

FIGS. 4A-4C depict a schematic see-through cross-sectional view of the double-walled elastomeric tube of the reversible valve assembly in a process of the reversible closure of the double-walled elastomeric tube. FIG. 4A shows the closed space 28 bordered by the outer tube 14, the inner tube 15, the first rotatable disk 17 and the second rotatable disk 7. FIG. 4B shows the closed space 28 in a twisted configuration upon the twisting of the double-walled elastomeric tube bordered by the outer tube 14 and the inner tube 15. Across the axial twist center 27, the closed space 28 in the twisted configuration is configured to be divided equally in half, and to be distended as the twisting of the double-walled elastomeric tube shrinks the closed space 28. Shown in FIG. 4C, the closed space 28 shrinks further with an increase in gas pressure inside the closed space 28 as the second rotatable disk 7 is fastened to the first rotatable disk 17. The increased gas pressure of the closed space 28 is transmitted centripetally to the axial twist center 27, concentrically squeezing further the axial twist center 27 in a way the axial twist center is rendered leakproof for both solid and liquid materials.

Figure 5A:
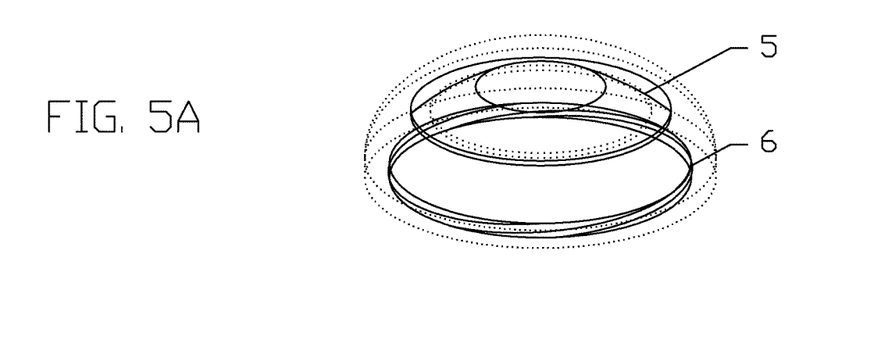
FIGS. 5A-5C show a schematic illustration of the components of the ostomy apparatus in a configuration having the cap (FIG. 5A), the reversible valve assembly in a closed configuration (FIG. 5B), and the base assembly (FIG. 5C).
Figure 5B:
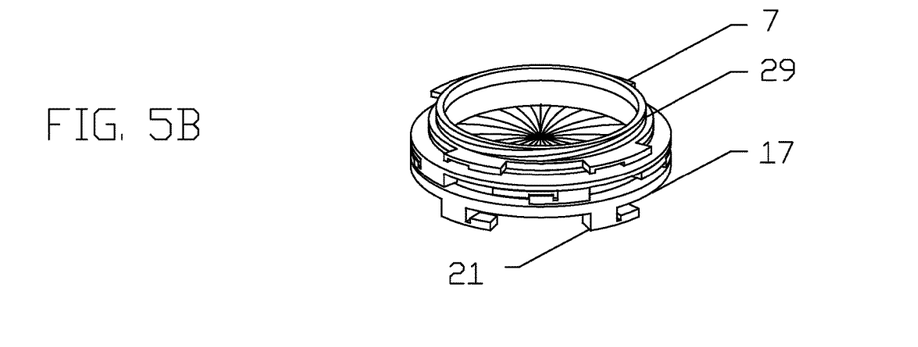
Figure 5C:
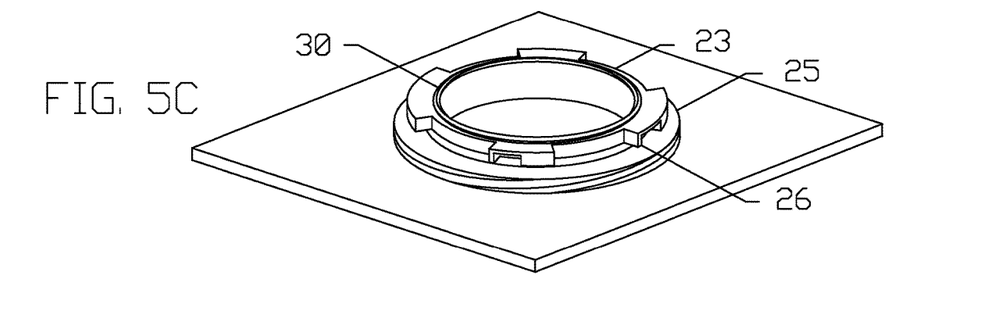

FIGS. 5A-5C show a schematic illustration of the components of the ostomy apparatus which is provided with the cap of FIG. 5A, the reversible valve assembly of FIG. 5B in the collapsed configuration, and the base assembly of FIG. 5C. The internal helical thread 5 is configured to mate with an external helical thread 29 of the reversible valve assembly of FIG. 5B. The external helical thread 29 is protuberantly disposed around an inner circular margin of the circular rim 10 of the reversible valve assembly, in a way the external helical thread 29 is rotatably insertable into the internal helical thread 5 of the cap of FIG. 5A. The ring-shaped internal helical thread 6 of the cap of FIG. 5A is configured to mate with the circular external helical thread 25 of the circular rim 23 of the base assembly of FIG. 5C. The internal helical thread 5 of the cap of FIG. 5A is also configured to mate with an external helical thread 30 of the base assembly of FIG. 5C. Referring to FIG. 2H, the external helical thread 30 is disposed on an outer surface of the O ring portion 24 of the base assembly of FIG. 5C in a way the external helical thread 30 is rotatably insertable into the internal helical thread 5 of the cap of FIG. 5A.

In a method of using the ostomy apparatus of the present invention, the base assembly of FIG. 5C is attached to an area of skin encircling an ostomy site of a patient. The male couplers 21 of the first rotatable disk 17 of the reversible valve assembly in the collapsed configuration of FIG. 5B mate with the female couplers 26 of the base assembly, in a way the reversible valve assembly of FIG. 5B is reversibly and sealably attached to the base assembly of FIG. 5C. The cap of FIG. 5A rotatably and fastenably covers the base assembly and the reversible valve assembly, wherein the ring-shaped internal helical thread 6 of the cap rotatably mates with the circular external helical thread 25 of the base assembly, and the internal helical thread 5 of the cap rotatably mates with the external helical thread 29 of the reversible valve assembly. If the patient feels a need to evacuate a biological material, first the ring-shaped internal helical thread 6 of the cap of FIG. 5A is rotatably released from the circular external helical thread 25 of the base assembly, wherein the rotatable release of the ring-shaped internal helical thread 6 of the cap from the circular external helical thread 25 of the base assembly is synchronized with rotatable release of the internal helical thread 5 of the cap from the external helical thread 29 of the reversible valve assembly. Following uncapping of the reversible valve assembly, the second rotatable disk 7 of the reversible valve assembly is rotatably unfastened from the first rotatable disk 17 of the reversible valve assembly and rotatably untwisted to revert to the open tubular configuration of the double-walled elastomeric tube of the reversible valve assembly. The open tubular configuration of the double-walled elastomeric tube of the reversible valve assembly allows the biological material to be evacuated through the double-walled elastomeric tube.

Figure 6A:
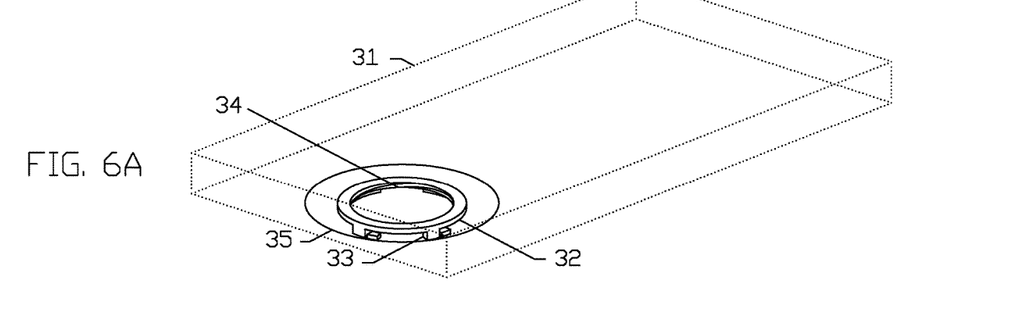
FIGS. 6A-6C show a schematic view of the components of the ostomy apparatus in a configuration having the collection bag (FIG. 6A), the reversible valve assembly in an open configuration (FIG. 6B), and the base assembly (FIG. 6C).
Figure 6B:
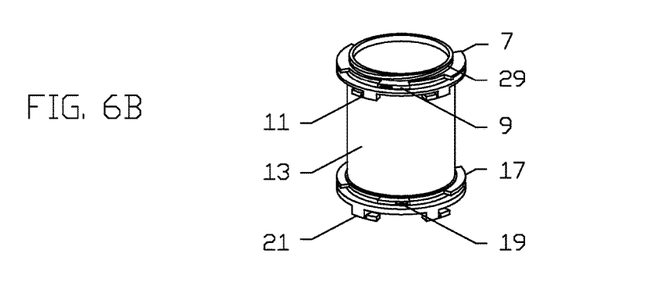
Figure 6C:
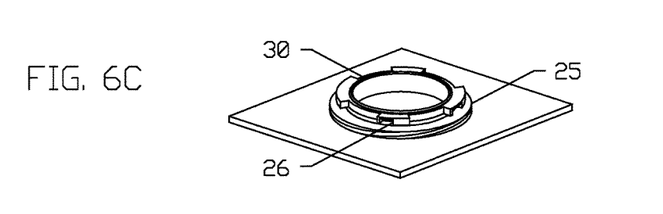

FIGS. 6A-6C show a schematic view of the components of the ostomy apparatus which is provided with the collection bag of FIG. 6A, the reversible valve assembly of FIG. 6B having the double-walled elastomeric tube in the untwisted and open configuration, and the base assembly of FIG. 6C. The collection bag of GIG. 6A comprises a collection pouch 31 having a circular opening on one side of the collection pouch, and a circular rim 32 attached to the circular opening via a circular flange 35. The circular rim 32 of the collection bag comprises a plurality of male couplers 33, and an internal helical thread 34 disposed on an inner surface of the circular rim 32. The plurality of male couplers 33 are configured to couple with the plurality of female couplers 9 of the second rotatable disk of the reversible valve assembly of FIG. 6B. The internal helical thread 34 of the collection bag of FIG. 6A is configured to mate with the external helical thread 29 of the second rotatable disk of the reversible valve assembly of FIG. 6B. The internal helical thread 34 of the collection bag of FIG. 6A is also configured to mate with the external helical thread 30 of the base assembly of FIG. 6C. Referring to FIG. 3C, the male coupler 11 of the second rotatable disk 7 is configured to reversibly and fastenably couple with the female coupler 19 of the first rotatable disk 17, shown in FIG. 6B. Referring to FIG. 3C, the plurality of male couplers 21 of the first rotatable disk 17 is configured to reversibly and fastenably couple with the female couplers 26 of the base assembly shown in FIG. 6C.

In another method of using the ostomy apparatus of the present invention, the base assembly of FIG. 6C is attached to an area of skin encircling an ostomy site of a patient. The male couplers 21 of the first rotatable disk 17 is reversibly and fastenably coupled with the female couplers 26 of the base assembly of FIG. 6C, in a way the reversible valve assembly of FIG. 6B is reversibly and sealably attached to the base assembly of FIG. 6C. The male couplers 33 of the collection bag of FIG. 6A is reversibly and sealably coupled with the female couplers 9 of the second rotatable disk 7 of FIG. 6B, in a way the collection bag of FIG. 6A is reversibly and sealably attached to the reversible valve assembly of FIG. 6B. Referring to FIG. 5B, the reversible valve assembly of FIG. 6B is provided in the twisted and closed configuration, wherein the second rotatable disk 7 is fastened to the collection bag of FIG. 6A, and wherein the first rotatable disk 17 is fastened to the base assembly of FIG. 6C. If the patient feels a need to evacuate a biological material, the male couplers 11 of the second rotatable disk 7 of the reversible valve assembly in the twisted and closed configuration are unfastened from the corresponding female couplers 19 of the first rotatable disk 17, wherein the unfastening of the second rotatable disk 7 from the first rotatable disk 17 reverts the double walled elastomeric tube 13 from the twisted and closed configuration to the open tubular configuration. The open tubular configuration of the double-walled elastomeric tube 13 of the reversible valve assembly allows the biological material to be evacuated through the double-walled elastomeric tube 13 into the collection bag of FIG. 6A.

It is to be understood that the aforementioned description of the apparatus is simple illustrative embodiments of the principles of the present invention. Various modifications and variations of the description of the present invention are expected to occur to those skilled in the art without departing from the spirit and scope of the present invention. Therefore the present invention is to be defined not by the aforementioned description but instead by the spirit and scope of the following claims.

What is claimed is:

1. An ostomy apparatus, comprising:
a base assembly, a reversible valve assembly, a cap, and a collection bag;
wherein the base assembly comprises an attachment sheet to skin, and a circular connecting rim having a central hole affixed coaxially to a corresponding central hole of the attachment sheet, wherein the attachment sheet of the base assembly is provided in a configuration to reversibly adhere to a skin around an ostomy site so as to resist a forward pressure of a biological material to the reversible valve assembly in a twisted and closed configuration without detachment of the attachment sheet from the skin, wherein the circular connecting rim of the base assembly is provided in a snap-in configuration to reversibly and sealably couple with a first rotatable disk of the reversible valve assembly, wherein the circular connecting rim of the base assembly is provided in the snap-in configuration to reversibly and sealably couple with a connecting port of the collection bag, and wherein the circular connecting rim of the base assembly is configured to reversibly and fastenably couple with the cap;

wherein the reversible valve assembly comprises a double-walled elastomeric tube fixedly connected to the first rotatable disk on one end and to a second rotatable disk on the other end of the double-walled elastomeric tube, wherein the rotatable disk is provided in a ring configuration, wherein the first rotatable disk is configured to reversibly and fastenably couple with and uncouple from the second rotatable disk, wherein the double-walled elastomeric tube is provided in a tube-in-tube configuration having a space between an outer tube and an inner tube, wherein the space in between the outer tube and the inner tube is configured to be a closed space, wherein the double-walled elastomeric tube is axially twistable along a longitudinal axis of the double-walled elastomeric tube, wherein a tubular lumen of the double-walled elastomeric tube is configured to be reversibly closed by the axial twisting of the double-walled elastomeric tube;

wherein the cap comprises an outer hemispherical bowel, a first internal helical thread disposed on an inner surface of a circumferential rim of the hemispherical bowel and a second internal helical thread disposed on an inner surface of an apical portion of the cap, wherein the cap is configured to reversibly close the reversible valve assembly by fastenable coupling of the second internal helical thread with the second rotatable disk of the reversible valve assembly, and wherein the cap is configured to reversibly close the base assembly by fastenable coupling of the first internal helical thread with the base assembly; and wherein the collection bag is provided with a plurality of female couplers on a circular rim of a connecting port of the collection bag, wherein the female couplers on the circular rim of the connecting port of the collection bag are configured to reversibly and sealably couple with male couplers of the second rotatable disk of the reversible valve assembly, and wherein the female couplers on the circular rim of the connecting port of the collection bag are configured to interchangeably couple with male couplers of the base assembly.

2. The ostomy apparatus according to claim 1, wherein the double-walled elastomeric tube of the reversible valve assembly further comprises:

the outer tube and the inner tube of the double-walled elastomeric tube are made of an elastomeric membrane, wherein the elastomeric membrane is configured to be stretchable and twistable; and the closed space in between the outer tube and the inner tube is configured to contain a gas having a gas pressure inside the closed space, wherein the axial twisting of the double-walled elastomeric tube is configured to increase the gas pressure inside the closed space by shrinking of a volume of the closed space, and wherein the increase in the gas pressure of the closed space in between the outer tube and the inner tube upon the axial twisting of the double-walled elastomeric tube is configured to be transmitted centripetally to an axial twisting center of the double-walled elastomeric tube so as to tighten the axial twisting center.

3. The ostomy apparatus according to claim 1, wherein the rotatable disk of the reversible valve assembly further comprises:

the rotatable disk provided in the ring configuration comprises a circular rim surrounding a hole, wherein the hole is open to and coaxially aligned with the tubular lumen of the double-walled elastomeric tube;

the reversible and fastenable coupling of the first rotatable disk with the second rotatable disk following several revolutions of the axial twisting of the double-walled elastomeric tube is configured to tightly encase the double-walled elastomeric tube of the reversible valve assembly in the twisted and closed configuration; and the uncoupling of the first rotatable disk from the second rotatable disk is configured to rotatably untwist the double-walled elastomeric tube in the twisted and closed configuration, wherein the untwisting of the double-walled elastomeric tube is configured to revert the double-walled elastomeric tube from the twisted and closed configuration to an open tubular configuration of the double-walled elastomeric tube so as to allow the biological material to be evacuated through the double-walled elastomeric tube.

4. A method of using an ostomy apparatus according to claim 1, comprising:

providing an ostomy apparatus comprising a base assembly, a reversible valve assembly, and a cap;

attaching the base assembly to an area of skin encircling an ostomy site of a patient;

reversibly and sealably coupling the reversible valve assembly with the base assembly, wherein the reversible valve assembly is provided in a twisted and closed configuration, and wherein the reversible valve assembly in the twisted and closed configuration comprises a first rotatable disk reversibly fastened to a second rotatable disk, wherein the reversible valve assembly in the twisted and closed configuration comprises a double-walled elastomeric tube in a twisted and closed configuration;

reversibly and fastenably capping the base assembly and the reversible valve assembly by the cap, wherein a first internal helical thread of the cap on an inner surface of a circumferential rim of the cap couples with the base assembly, and wherein a second internal helical thread of the cap on an inner surface of an apical portion of the cap couples with the second rotatable disk of the reversible valve assembly;

uncapping the cap from the base assembly and the reversible valve assembly, wherein the first internal helical thread of the cap uncouples from the base assembly, and wherein the second internal helical thread of the cap uncouples from the second rotatable disk of the reversible valve assembly;

uncoupling the second rotatable disk from the first rotatable disk of the reversible valve assembly and untwisting the double-walled elastomeric tube from the twisted and closed configuration of the double-walled elastomeric tube, wherein the untwisting of the double-walled elastomeric tube reverts the double-walled elastomeric tube from the twisted and closed configuration to an open tubular configuration of the double-walled elastomeric tube;

letting a biological material evacuated through the double-walled elastomeric tube in the open tubular configuration;

twisting the second rotatable disk of the reversible valve assembly so as to axially twist the double-walled elastomeric tube along a longitudinal axis of the double-walled elastomeric tube, wherein the axial twisting of the double-walled elastomeric tube reversibly closes a tubular lumen of the double-walled elastomeric tube, and wherein the axial twisting of the double-walled elastomeric tube increases a gas pressure inside a closed space in between an outer tube and an inner tube of the double-walled elastomeric tube so as to tighten an axial twisting center of the double-walled elastomeric tube;

reversibly and fastenably coupling the second rotatable disk with the first rotatable disk of the reversible valve assembly, wherein the reversible and fastenable coupling of the second rotatable disk with the first rotatable disk tightly encases the double-walled elastomeric tube of the reversible valve assembly in the twisted and closed configuration; and reversibly and fastenably capping the base assembly and the reversible valve assembly by the cap, wherein the first internal helical thread of the cap on the inner surface of the circumferential rim of the cap couples with the base assembly, and wherein the second internal helical thread of the cap on the inner surface of the apical portion of the cap couples with the second rotatable disk of the reversible valve assembly.

5. A method of using an ostomy apparatus according to claim 1, comprising:

providing an ostomy apparatus comprising a base assembly, a reversible valve assembly, and a collection bag;

attaching the base assembly to an area of skin encircling an ostomy site of a patient;

reversibly and sealably coupling the reversible valve assembly with the base assembly, wherein the reversible valve assembly is provided in a twisted and closed configuration, and wherein the reversible valve assembly in the twisted and closed configuration comprises a first rotatable disk reversibly fastened to a second rotatable disk, wherein the reversible valve assembly in the twisted and closed configuration comprises a double-walled elastomeric tube in a twisted and closed configuration;

reversibly and sealably coupling a connecting port of the collection bag with the reversible valve assembly, wherein female couplers on a circular rim of the connecting port of the collection bag couple with male couplers of the second rotatable disk of the reversible valve assembly;

uncoupling the second rotatable disk from the first rotatable disk of the reversible valve assembly and untwisting the double-walled elastomeric tube from the twisted and closed configuration of the double-walled elastomeric tube, wherein the untwisting of the double-walled elastomeric tube reverts the double-walled elastomeric tube from the twisted and closed configuration to an open tubular configuration of the double-walled elastomeric tube;

letting a biological material evacuated through the double-walled elastomeric tube in the open tubular configuration into the collection bag;

twisting the second rotatable disk of the reversible valve assembly so as to axially twist the double-walled elastomeric tube along a longitudinal axis of the double-walled elastomeric tube, wherein the axial twisting of the double-walled elastomeric tube reversibly closes a tubular lumen of the double-walled elastomeric tube, and wherein the axial twisting of the double-walled elastomeric tube increases a gas pressure inside a closed space in between an outer tube and an inner tube of the double-walled elastomeric tube so as to tighten an axial twisting center of the double-walled elastomeric tube; and reversibly and fastenably coupling the second rotatable disk with the first rotatable disk of the reversible valve assembly, wherein the reversible and fastenable coupling of the second rotatable disk with the first rotatable disk tightly encases the double-walled elastomeric tube of the reversible valve assembly in the twisted and closed configuration.

* * * * *